US009265811B2

(12) United States Patent
Paterson et al.

(10) Patent No.: US 9,265,811 B2
(45) Date of Patent: Feb. 23, 2016

(54) FORMULATIONS FOR A TIGHT JUNCTION EFFECTOR

(75) Inventors: Blake Paterson, Baltimore, MD (US); Mark J. Ginski, Perry, MD (US)

(73) Assignee: ALBA THERAPEUTICS CORPORATION, Baltimore, MD (US)

(*) Notice: Subject to any disclaimer, the term of this patent is extended or adjusted under 35 U.S.C. 154(b) by 1576 days.

(21) Appl. No.: 11/673,342

(22) Filed: Feb. 9, 2007

(65) Prior Publication Data
US 2007/0196501 A1 Aug. 23, 2007

Related U.S. Application Data

(60) Provisional application No. 60/771,454, filed on Feb. 9, 2006.

(51) Int. Cl.
*A61K 38/08* (2006.01)
*A61K 31/175* (2006.01)
*A61K 31/426* (2006.01)
*A61K 38/00* (2006.01)
*A61K 9/14* (2006.01)
*A61K 9/20* (2006.01)
*A61K 9/16* (2006.01)
*A61K 9/48* (2006.01)
*A61K 9/00* (2006.01)
*A61K 9/50* (2006.01)

(52) U.S. Cl.
CPC . *A61K 38/08* (2013.01); *A61K 9/14* (2013.01); *A61K 9/1635* (2013.01); *A61K 9/1652* (2013.01); *A61K 9/1676* (2013.01); *A61K 9/20* (2013.01); *A61K 9/4808* (2013.01); *A61K 9/5078* (2013.01); *A61K 31/175* (2013.01); *A61K 31/426* (2013.01); *A61K 9/009* (2013.01); *A61K 9/5026* (2013.01); *A61K 9/5036* (2013.01); *A61K 9/5042* (2013.01); *A61K 9/5047* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 5,643,602 A | 7/1997 | Ulmius | |
| 5,827,534 A | 10/1998 | Fasano | |
| 5,864,014 A | 1/1999 | Fasano | |
| 5,912,323 A | 6/1999 | Fasano | |
| 5,945,510 A | 8/1999 | Fasano | |
| 5,948,629 A | 9/1999 | Fasano | |
| 6,458,925 B1 * | 10/2002 | Fasano | 530/328 |
| 6,506,577 B1 | 1/2003 | Deming et al. | |
| 6,670,448 B2 | 12/2003 | Fasano | |
| 6,733,762 B1 | 5/2004 | Fasano et al. | |
| 6,793,936 B2 * | 9/2004 | Devane et al. | 424/484 |
| 6,936,689 B2 | 8/2005 | Fasano | |
| 7,026,294 B2 | 4/2006 | Fasano et al. | |
| 7,189,696 B2 | 3/2007 | Fasano | |
| 7,294,689 B2 | 11/2007 | Fasano et al. | |
| 7,531,504 B2 | 5/2009 | Fasano | |
| 7,531,512 B2 | 5/2009 | Fasano et al. | |
| 7,582,603 B2 | 9/2009 | Fasano | |
| 2002/0094346 A1 | 7/2002 | Lin | |
| 2003/0152627 A1 | 8/2003 | Beckert et al. | |
| 2003/0180352 A1 * | 9/2003 | Patel et al. | 424/465 |
| 2005/0249807 A1 | 11/2005 | Brown et al. | |
| 2006/0269968 A1 | 11/2006 | Fasano | |
| 2008/0103100 A1 | 5/2008 | Fasano et al. | |
| 2009/0069247 A1 | 3/2009 | Patterson et al. | |

FOREIGN PATENT DOCUMENTS

| | | | |
|---|---|---|---|
| EP | 0 557 897 | 9/1993 | |
| EP | 0 675 199 | 10/1995 | |
| GB | WO 2004/004696 | * 1/2004 | A61K 9/50 |
| JP | 2004-517156 | 6/2004 | |
| WO | WO9411508 | 5/1994 | |
| WO | WO9733909 | 9/1997 | |
| WO | WO9837096 | 8/1998 | |
| WO | WO9852415 | 11/1998 | |
| WO | WO0189551 | 11/2001 | |

OTHER PUBLICATIONS

Clemente et al. In Gastroenterology 126(4), Suppl. 2, p. A249 (Apr. 2004).*
Fasano in Physiological Reviews, 91, 151-175 (2011).*
Motlekar et al. In Journal of Drug Targeting 14(5):321-329 (2006).*
Fasano, "Biological Perspectives: Physiological, Pathological, and Therapeutic Implications of Zonulin-Mediated Intestinal Barrier Modulation- Living Life on the Edge of the Wall", The American Journal of Pathology, Nov. 2008, vol. 173, No. 5, pp. 1243-1252.
Pizzuti et al., "Transcriptional downregulation of tight junction protein ZO-1 in active coeliac diseas is reversed after a gluten-free diet", Digestive and Liver Disease, May 2004, vol. 36(5), pp. 337-341.
Fasano et al., "The Role of the Intestinal Barrier Function in the Pathogenesis of Celiac Disease—Frontiers in Celiac Disease". Pediatric Adolescent Medicine Basel, Karger, 2008, vol. 12, pp. 89-98.
Fasano, "Surprises from Celiac Disease", Scientific American, Aug. 2009, vol. 301(2), pp. 54-61.
Clayburgh et al., "A porous defense: the leaky epithelial barrier in intestinal disease", Laboratory Investigation, 2004, vol. 84, pp. 282-291.
Wang et al., "Human zonulin, a potential modulator of intestinal tight junctions", Journal of Cell Science, 2000, vol. 113, pp. 4435-4440.

(Continued)

*Primary Examiner* — Dennis Heyer
(74) *Attorney, Agent, or Firm* — Morgan, Lewis & Bockius LLP

(57) ABSTRACT

Enteric compositions comprising one or more tight junction agonists and/or one or more tight junction antagonists are provided. Compositions of the invention may comprise a delayed-release coating disposed over a tight junction agonist and/or tight junction antagonist layer which may be disposed over an inert core. Delayed-release coatings may be substantially stable in gastric fluid and substantially unstable in intestinal fluid, thus providing for substantial release of the tight junction agonist and/or antagonist from the composition in the duodenum or jejunum of the small intestine.

28 Claims, 1 Drawing Sheet

(56) References Cited

OTHER PUBLICATIONS

Holmes et al., "Claudin profiling in the mouse during postnatal intestinal development and along the gastrointestinal tract reveals complex expression patterns", Gene Expression Patterns, 2006, vol. 6, pp. 581-588.
Murray, "The widening spectrum of celiac disease", Am. J. Clin. Nutr., 1999, vol. 69, pp. 354-365.
Chiarioni et al., "Gluten-Free Diet Normalizes Mouth-to-Cecum Transit of a Caloric Meal in Adult Patients with Celiac Disease", Digestive Diseases and Sciences, Oct. 1997, vol. 42, No. 10, pp. 2100-2105.
Deli, "Potential use of tight junction modulators to reversibly open membranous barriers and improve drug delivery", Biochemica et Biophysica Acta, 2009, 1788, pp. 892-910.
Fasano et al., "Zonulin, a newly discovered modulator of intestinal permeability, and its expression in coeliac disease", The Lancet, Apr. 2000, vol. 355, pp. 1518-1519.
Ewe et al., "Inflammation Does Not Decrease Intraluminal pH in Chronic Inflammatory Bowel Disease", Digestive Diseases and Sciences, Jul. 1999, vol. 44, No. 7, pp. 1434-1439.
Sadik et al., "Gut Transit in Celiac Disease: Delay of Small Bowel Transit and Acceleration after Dietary Treatment", American Journal of Gastroenterology, Dec. 2004, vol. 99, No. 12, pp. 2429-2436.
McConnell et al., "Gut instincts: Explorations in intestinal physiology and drug delivery", International Journal of Pharmaceutics, Dec. 2008, vol. 364, No. 2, pp. 213-226.
Sapone et al., "Zonulin Upregulation is Associated With Increased Gut Permeability in Subjects With Type 1 Diabetes and Their Relatives", Diabetes, May 2006, vol. 55, pp. 1443-1449.
Watts et al., "Role of the intestinal tight junction modulator zonulin in the pathogenesis of type 1 diabetes in BB diabetic-prone rates", PNAS, Feb. 2005, vol. 102, No. 8, pp. 2916-2921.
Di Sabatino et al., "Coeliac Disease", The Lancet, Apr. 2009, vol. 373, pp. 1480-1493.
Fasano et al., "Mechanisms of Disease: the role of intestinal barrier function in the pathogenesis of gastrointestinal autoimmune diseases", Nature Clinical Practice Gastroenterology & Hepatology, Sep. 2005, vol. 2, No. 9, pp. 416-422.
Arhewoh et al., "Optimising oral systems for the delivery of therapeutic proteins and peptides", African Journal of Biotechnology, Dec. 2005, vol. 4(13), pp. 1591-1597.
Ciccocioppo et al., "Altered Expression, Localization, and Phosphorylation of Epithelial Junction Proteins in Celiac Disease", American Journal of Clinical Pathology, 2006, vol. 125, pp. 502-511.
Rohm Deguss-Huls NEWS, Pharma Polymers, Oct. 2000, No. 7, pp. 1-6.
Clemente et al., "Early effects of gliadin on enterocyte intracellular signalling involved in intestinal barrier function", Gut, 2003, vol. 52, pp. 218-223.
Teahon et al., "Assessing the site of increased intestinal permeability in coeliac and inflammatory bowel disease", Gut, 1996, vol. 38, pp. 864-869.
International Search Report issued in Appl. No. PCT/US2007/003486 on Jul. 11, 2008, 4 pages.
Baudry et al., "Cloning of a Gene (zot) Encoding a New Toxin Produced by Vibrio cholerae", Infection and Immunity, Feb. 1992, vol. 60, No. 2., pp. 428-434.
Bolton et al., "Loss of the tight junction proteins occludin and zonula occludens-1 from cerebral vascular endothelium during neutrophil-induced blood-brain barrier breakdown in vivo", 1998, Neuroscience, vol. 86, No. 4, pp. 1245-1257.
Jeppsson et al., "Blood-brain barrier derangement in Uremic encephalopathy", Jul. 1982, Surgery, vol. 92, No. 1, 1 page.
Supplementary European Search Report for European Application No. 07750332.4, mailed Jul. 18, 2012, 5 pages.
"Duodenum," MedlinePlus Medical Encyclopedia, Retrieved from the Internet: <http://www.nlm.nih.gov/medlineplus/ency/article/002347.htm>, Retrieved on May 9, 2011, 1 page.
"Ileum," Wikipedia, Retrieved from the Internet: <http://en.wikipedia.org/wiki/ileum>, Retrieved on Oct. 11, 2012, 4 pages.
Morishita, I. et al, "Controlled release microspheres based on eudragit L100 for the oral administration of erythromycin," Drug Design and Delivery, 7:309-319 (1991).
Thoma, K. et al, "The solubility kinetics of enteric-resistant tablets using riboflavin test tablets. 6. Pharmaceutic-technologic and analytic studies on gastric juice-resistant dosage forms," Pharmazine, 46(5):331-336 (1991) (with English Abstract).
Tripathi, A. et al, "Identification of human zonulin, a physiological modulator of tight junctions, as prehaptoglobin-2," PNAS, 106(39):16799-16804 (2009).
Vantini, I. et al, "In vitro study of a new pancreatic enzyme with high lipase content in enteric coated microtablets," Clinica Terapeutica, 142:445-451 (1993) (with English Abstract).
Yoshitomi, H. et al, "Evaluation of enteric coated tablet sensitive to pancreatic lipase. I. In vitro disintegration test," Chem. Pharm. Bull., 40(7):1902-1905 (1992).

* cited by examiner

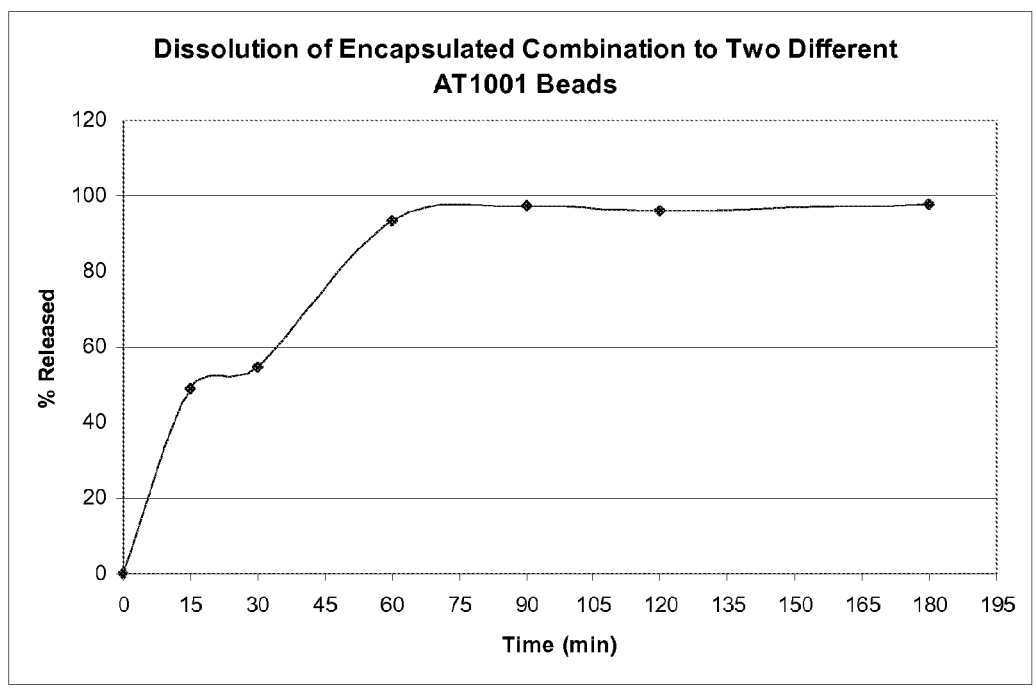

SEQUENCE LISTING

```
<160> NUMBER OF SEQ ID NOS: 47

<210> SEQ ID NO 1
<211> LENGTH: 8
<212> TYPE: PRT
<213> ORGANISM: Artificial
<220> FEATURE:
<223> OTHER INFORMATION: Chemically synthesized

<400> SEQUENCE: 1

Gly Gly Val Leu Val Gln Pro Gly
1               5
```

```
<210> SEQ ID NO 2
<211> LENGTH: 6
<212> TYPE: PRT
<213> ORGANISM: Artificial
<220> FEATURE:
<223> OTHER INFORMATION: Chemically synthesized

<400> SEQUENCE: 2

Phe Cys Ile Gly Arg Leu
1               5

<210> SEQ ID NO 3
<211> LENGTH: 8
<212> TYPE: PRT
<213> ORGANISM: Artificial
<220> FEATURE:
<223> OTHER INFORMATION: Chemically synthesized

<400> SEQUENCE: 3

Gly Arg Val Cys Val Gln Pro Gly
1               5

<210> SEQ ID NO 4
<211> LENGTH: 8
<212> TYPE: PRT
<213> ORGANISM: Artificial
<220> FEATURE:
<223> OTHER INFORMATION: Chemically synthesized

<400> SEQUENCE: 4

Gly Arg Val Cys Val Gln Asp Gly
1               5

<210> SEQ ID NO 5
<211> LENGTH: 8
<212> TYPE: PRT
<213> ORGANISM: Artificial
<220> FEATURE:
<223> OTHER INFORMATION: Chemically synthesized

<400> SEQUENCE: 5

Gly Arg Val Leu Val Gln Pro Gly
1               5

<210> SEQ ID NO 6
<211> LENGTH: 8
<212> TYPE: PRT
<213> ORGANISM: Artificial
<220> FEATURE:
<223> OTHER INFORMATION: Chemically synthesized

<400> SEQUENCE: 6

Gly Arg Val Leu Val Gln Asp Gly
1               5

<210> SEQ ID NO 7
<211> LENGTH: 8
<212> TYPE: PRT
<213> ORGANISM: Artificial
<220> FEATURE:
<223> OTHER INFORMATION: Chemically synthesized

<400> SEQUENCE: 7

Gly Arg Leu Cys Val Gln Pro Gly
1               5
```

```
<210> SEQ ID NO 8
<211> LENGTH: 8
<212> TYPE: PRT
<213> ORGANISM: Artificial
<220> FEATURE:
<223> OTHER INFORMATION: Chemically synthesized

<400> SEQUENCE: 8

Gly Arg Leu Cys Val Gln Asp Gly
1               5

<210> SEQ ID NO 9
<211> LENGTH: 8
<212> TYPE: PRT
<213> ORGANISM: Artificial
<220> FEATURE:
<223> OTHER INFORMATION: Chemically synthesized

<400> SEQUENCE: 9

Gly Arg Leu Leu Val Gln Pro Gly
1               5

<210> SEQ ID NO 10
<211> LENGTH: 8
<212> TYPE: PRT
<213> ORGANISM: Artificial
<220> FEATURE:
<223> OTHER INFORMATION: Chemically synthesized

<400> SEQUENCE: 10

Gly Arg Leu Leu Val Gln Asp Gly
1               5

<210> SEQ ID NO 11
<211> LENGTH: 8
<212> TYPE: PRT
<213> ORGANISM: Artificial
<220> FEATURE:
<223> OTHER INFORMATION: Chemically synthesized

<400> SEQUENCE: 11

Gly Arg Gly Cys Val Gln Pro Gly
1               5

<210> SEQ ID NO 12
<211> LENGTH: 8
<212> TYPE: PRT
<213> ORGANISM: Artificial
<220> FEATURE:
<223> OTHER INFORMATION: Chemically synthesized

<400> SEQUENCE: 12

Gly Arg Gly Cys Val Gln Asp Gly
1               5

<210> SEQ ID NO 13
<211> LENGTH: 8
<212> TYPE: PRT
<213> ORGANISM: Artificial
<220> FEATURE:
<223> OTHER INFORMATION: Chemically synthesized

<400> SEQUENCE: 13

Gly Arg Gly Leu Val Gln Pro Gly
1               5
```

```
<210> SEQ ID NO 14
<211> LENGTH: 8
<212> TYPE: PRT
<213> ORGANISM: Artificial
<220> FEATURE:
<223> OTHER INFORMATION: Chemically synthesized

<400> SEQUENCE: 14

Gly Arg Gly Leu Val Gln Asp Gly
1               5

<210> SEQ ID NO 15
<211> LENGTH: 8
<212> TYPE: PRT
<213> ORGANISM: Artificial
<220> FEATURE:
<223> OTHER INFORMATION: Chemically synthesized

<400> SEQUENCE: 15

Gly Gly Val Cys Val Gln Pro Gly
1               5

<210> SEQ ID NO 16
<211> LENGTH: 8
<212> TYPE: PRT
<213> ORGANISM: Artificial
<220> FEATURE:
<223> OTHER INFORMATION: Chemically synthesized

<400> SEQUENCE: 16

Gly Gly Val Cys Val Gln Asp Gly
1               5

<210> SEQ ID NO 17
<211> LENGTH: 8
<212> TYPE: PRT
<213> ORGANISM: Artificial
<220> FEATURE:
<223> OTHER INFORMATION: Chemically synthesized

<400> SEQUENCE: 17

Gly Gly Val Leu Val Gln Asp Gly
1               5

<210> SEQ ID NO 18
<211> LENGTH: 8
<212> TYPE: PRT
<213> ORGANISM: Artificial
<220> FEATURE:
<223> OTHER INFORMATION: Chemically synthesized

<400> SEQUENCE: 18

Gly Gly Leu Cys Val Gln Pro Gly
1               5

<210> SEQ ID NO 19
<211> LENGTH: 8
<212> TYPE: PRT
<213> ORGANISM: Artificial
<220> FEATURE:
<223> OTHER INFORMATION: Chemically synthesized

<400> SEQUENCE: 19

Gly Gly Leu Cys Val Gln Asp Gly
1               5
```

```
<210> SEQ ID NO 20
<211> LENGTH: 8
<212> TYPE: PRT
<213> ORGANISM: Artificial
<220> FEATURE:
<223> OTHER INFORMATION: Chemically synthesized

<400> SEQUENCE: 20

Gly Gly Leu Leu Val Gln Pro Gly
1               5

<210> SEQ ID NO 21
<211> LENGTH: 8
<212> TYPE: PRT
<213> ORGANISM: Artificial
<220> FEATURE:
<223> OTHER INFORMATION: Chemically synthesized

<400> SEQUENCE: 21

Gly Gly Leu Leu Val Gln Asp Gly
1               5

<210> SEQ ID NO 22
<211> LENGTH: 8
<212> TYPE: PRT
<213> ORGANISM: Artificial
<220> FEATURE:
<223> OTHER INFORMATION: Chemically synthesized

<400> SEQUENCE: 22

Gly Gly Gly Cys Val Gln Pro Gly
1               5

<210> SEQ ID NO 23
<211> LENGTH: 8
<212> TYPE: PRT
<213> ORGANISM: Artificial
<220> FEATURE:
<223> OTHER INFORMATION: Chemically synthesized

<400> SEQUENCE: 23

Gly Gly Gly Cys Val Gln Asp Gly
1               5

<210> SEQ ID NO 24
<211> LENGTH: 8
<212> TYPE: PRT
<213> ORGANISM: Artificial
<220> FEATURE:
<223> OTHER INFORMATION: Chemically synthesized

<400> SEQUENCE: 24

Gly Gly Gly Leu Val Gln Pro Gly
1               5

<210> SEQ ID NO 25
<211> LENGTH: 8
<212> TYPE: PRT
<213> ORGANISM: Artificial
<220> FEATURE:
<223> OTHER INFORMATION: Chemically synthesized

<400> SEQUENCE: 25

Gly Gly Gly Leu Val Gln Asp Gly
1               5
```

-continued

```
<210> SEQ ID NO 26
<211> LENGTH: 8
<212> TYPE: PRT
<213> ORGANISM: Artificial
<220> FEATURE:
<223> OTHER INFORMATION: Chemically synthesized

<400> SEQUENCE: 26

Val Asp Gly Phe Gly Arg Ile Gly
1               5

<210> SEQ ID NO 27
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Xaa can be Ala, Val, Leu, Ile, Pro, Trp, Tyr,
      and Met

<400> SEQUENCE: 27

Xaa Cys Ile Gly Arg Leu
1               5

<210> SEQ ID NO 28
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (2)..(2)
<223> OTHER INFORMATION: Xaa can be Gly, Ser, Thr, Tyr, Asn, and Gln

<400> SEQUENCE: 28

Phe Xaa Ile Gly Arg Leu
1               5

<210> SEQ ID NO 29
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: Xaa can be Ala, Val, Leu, Ile, Pro, Trp, and
      Met

<400> SEQUENCE: 29

Phe Cys Xaa Gly Arg Leu
1               5

<210> SEQ ID NO 30
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (4)..(4)
<223> OTHER INFORMATION: Xaa can be Gly, Ser, Thr, Tyr, Asn, Ala, and
      Gln
```

```
<400> SEQUENCE: 30

Phe Cys Ile Xaa Arg Leu
1               5

<210> SEQ ID NO 31
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (5)..(5)
<223> OTHER INFORMATION: Xaa can be Lys and His

<400> SEQUENCE: 31

Phe Cys Ile Gly Xaa Leu
1               5

<210> SEQ ID NO 32
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (6)..(6)
<223> OTHER INFORMATION: Xaa can be Ala, Val, Leu, Ile, Pro, Trp, and
      Met

<400> SEQUENCE: 32

Phe Cys Ile Gly Arg Xaa
1               5

<210> SEQ ID NO 33
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Xaa can be Ala, Val, Leu, Ile, Pro, Trp, Tyr,
      and Met
<220> FEATURE:
<221> NAME/KEY: misc_feature
<222> LOCATION: (2)..(2)
<223> OTHER INFORMATION: Xaa can be Gly, Ser, Thr, Tyr, Asn, and Gln

<400> SEQUENCE: 33

Xaa Xaa Ile Gly Arg Leu
1               5

<210> SEQ ID NO 34
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Xaa can be Ala, Val, Leu, Ile, Pro, Trp, Tyr,
      and Met
<220> FEATURE:
<221> NAME/KEY: misc_feature
<222> LOCATION: (3)..(3)
<223> OTHER INFORMATION: Xaa can be Ala, Val, Leu, Ile, Pro, Trp, and
      Met
```

```
<400> SEQUENCE: 34

Xaa Cys Xaa Gly Arg Leu
1               5

<210> SEQ ID NO 35
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Xaa can be Ala, Val, Leu, Ile, Pro, Trp, Tyr,
      and Met
<220> FEATURE:
<221> NAME/KEY: misc_feature
<222> LOCATION: (4)..(4)
<223> OTHER INFORMATION: Xaa can be Gly, Ser, Thr, Tyr, Asn, Ala, and
      Gln

<400> SEQUENCE: 35

Xaa Cys Ile Xaa Arg Leu
1               5

<210> SEQ ID NO 36
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Xaa can be Ala, Val, Leu, Ile, Pro, Trp, Tyr,
      and Met
<220> FEATURE:
<221> NAME/KEY: misc_feature
<222> LOCATION: (5)..(5)
<223> OTHER INFORMATION: Xaa can be Lys and His

<400> SEQUENCE: 36

Xaa Cys Ile Gly Xaa Leu
1               5

<210> SEQ ID NO 37
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (1)..(1)
<223> OTHER INFORMATION: Xaa can be Ala, Val, Leu, Ile, Pro, Trp, Tyr,
      and Met
<220> FEATURE:
<221> NAME/KEY: misc_feature
<222> LOCATION: (6)..(6)
<223> OTHER INFORMATION: Xaa can be Ala, Val, Leu, Ile, Pro, Trp, and
      Met

<400> SEQUENCE: 37

Xaa Cys Ile Gly Arg Xaa
1               5

<210> SEQ ID NO 38
<211> LENGTH: 6
<212> TYPE: PRT
<213> ORGANISM: Artificial
```

```
<220> FEATURE:
<223> OTHER INFORMATION: synthetic peptide
<220> FEATURE:
<221> NAME/KEY: misc_feature
<222> LOCATION: (2)..(2)
<223> OTHER INFORMATION: Xaa can be Gly, Ser, Thr, Tyr, Asn, and Gln
<220> FEATURE:
<221> NAME/KEY: misc_feature
<222> LOCATION: (3)..(3)
<223> OTHER INFORMATION: Xaa can be Ala, Val, Leu, Ile, Pro, Trp, and
      Met

<400> SEQUENCE: 38

Phe Xaa Xaa Gly Arg Leu
1               5

<210> SEQ ID NO 39
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (2)..(2)
<223> OTHER INFORMATION: Xaa can be Gly, Ser, Thr, Tyr, Asn, and Gln
<220> FEATURE:
<221> NAME/KEY: misc_feature
<222> LOCATION: (4)..(4)
<223> OTHER INFORMATION: Xaa can be Gly, Ser, Thr, Tyr, Asn, Ala, and
      Gln

<400> SEQUENCE: 39

Phe Xaa Ile Xaa Arg Leu
1               5

<210> SEQ ID NO 40
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (2)..(2)
<223> OTHER INFORMATION: Xaa can be Gly, Ser, Thr, Tyr, Asn, and Gln
<220> FEATURE:
<221> NAME/KEY: misc_feature
<222> LOCATION: (5)..(5)
<223> OTHER INFORMATION: Xaa can be Lys and His

<400> SEQUENCE: 40

Phe Xaa Ile Gly Xaa Leu
1               5

<210> SEQ ID NO 41
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (2)..(2)
<223> OTHER INFORMATION: Xaa can be Gly, Ser, Thr, Tyr, Asn, and Gln
<220> FEATURE:
<221> NAME/KEY: misc_feature
<222> LOCATION: (6)..(6)
<223> OTHER INFORMATION: Xaa can be Ala, Val, Leu, Ile, Pro, Trp, and
      Met
```

```
<400> SEQUENCE: 41

Phe Xaa Ile Gly Arg Xaa
1               5

<210> SEQ ID NO 42
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: Xaa can be Ala, Val, Leu, Ile, Pro, Trp, and
      Met
<220> FEATURE:
<221> NAME/KEY: misc_feature
<222> LOCATION: (4)..(4)
<223> OTHER INFORMATION: Xaa can be Gly, Ser, Thr, Tyr, Asn, Ala, and
      Gln

<400> SEQUENCE: 42

Phe Cys Xaa Xaa Arg Leu
1               5

<210> SEQ ID NO 43
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: Xaa can be Ala, Val, Leu, Ile, Pro, Trp, and
      Met
<220> FEATURE:
<221> NAME/KEY: misc_feature
<222> LOCATION: (5)..(5)
<223> OTHER INFORMATION: Xaa can be Lys and His

<400> SEQUENCE: 43

Phe Cys Xaa Gly Xaa Leu
1               5

<210> SEQ ID NO 44
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (3)..(3)
<223> OTHER INFORMATION: Xaa can be Ala, Val, Leu, Ile, Pro, Trp, and
      Met
<220> FEATURE:
<221> NAME/KEY: misc_feature
<222> LOCATION: (6)..(6)
<223> OTHER INFORMATION: Xaa can be Ala, Val, Leu, Ile, Pro, Trp, and
      Met

<400> SEQUENCE: 44

Phe Cys Xaa Gly Arg Xaa
1               5

<210> SEQ ID NO 45
<211> LENGTH: 6
<212> TYPE: PRT
<213> ORGANISM: Artificial
```

```
<220> FEATURE:
<223> OTHER INFORMATION: Chemically synthesized
<220> FEATURE:
<221> NAME/KEY: misc_feature
<222> LOCATION: (4)..(4)
<223> OTHER INFORMATION: Xaa can be Gly, Ser, Thr, Tyr, Asn, Ala, and
      Gln
<220> FEATURE:
<221> NAME/KEY: misc_feature
<222> LOCATION: (5)..(5)
<223> OTHER INFORMATION: Xaa can be Lys and His

<400> SEQUENCE: 45

Phe Cys Ile Xaa Xaa Leu
1               5

<210> SEQ ID NO 46
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (4)..(4)
<223> OTHER INFORMATION: Xaa can be Gly, Ser, Thr, Tyr, Asn, Ala, and
      Gln
<220> FEATURE:
<221> NAME/KEY: misc_feature
<222> LOCATION: (6)..(6)
<223> OTHER INFORMATION: Xaa can be Ala, Val, Leu, Ile, Pro, Trp, and
      Met

<400> SEQUENCE: 46

Phe Cys Ile Xaa Arg Xaa
1               5

<210> SEQ ID NO 47
<211> LENGTH: 6
<212> TYPE: PRT
<213> ORGANISM: Artificial
<220> FEATURE:
<223> OTHER INFORMATION: Chemically synthesized
<220> FEATURE:
<221> NAME/KEY: misc_feature
<222> LOCATION: (5)..(5)
<223> OTHER INFORMATION: Xaa can be Lys and His
<220> FEATURE:
<221> NAME/KEY: misc_feature
<222> LOCATION: (6)..(6)
<223> OTHER INFORMATION: Xaa can be Ala, Val, Leu, Ile, Pro, Trp, and
      Met

<400> SEQUENCE: 47

Phe Cys Ile Gly Xaa Xaa
1               5
```

FORMULATIONS FOR A TIGHT JUNCTION EFFECTOR

CROSS REFERENCE TO RELATED APPLICATIONS

This application claims priority to U.S. provisional patent application Ser. No. 60/771,454, filed Feb. 9, 2006, the entire contents of which are specifically incorporated herein by reference.

STATEMENT REGARDING FEDERALLY SPONSORED RESEARCH

The subject matter of this application was in part funded by the National Institutes of Health grant no. 1 R41 DK074316-01. The United States Government has certain rights in this application.

FIELD OF THE INVENTION

The present invention includes pharmaceutical dosage forms comprising certain tight junction antagonists or agonists and an enteric coating.

BACKGROUND OF THE INVENTION

Intestinal tight junction dysfunction occurs in a variety of clinical conditions, including food allergies, infections of the gastrointestinal tract, autoimmune diseases, and inflammatory bowel diseases. Healthy, mature gut mucosa with its intact tight junction serves as the main barrier to the passage of macromolecules. During the healthy state, small quantities of immunologically active proteins cross the gut host barrier. These proteins are absorbed across the mucosa through at least two pathways. The vast majority of absorbed proteins (up to 90%) cross the intestinal barrier via the transcellular pathway, followed by lysosomal degradation that converts proteins into smaller, non-immunogenic peptides. Other proteins are transported as intact proteins, through the paracellular pathway, which involves a subtle but sophisticated regulation of intercellular tight junctions that lead to protein (antigen) tolerance. When the integrity of the tight junction system is compromised, as with prematurity or after exposure to radiation, chemotherapy, and/or toxins, a deleterious response to environmental antigens (including autoimmune diseases and food allergies) can occur.

To meet the many diverse physiological and pathological challenges to which epithelia are subjected, the tight junctions or zonula occludens (ZO) must be capable of rapid, physiologic, reversible, transient, energy dependent, and coordinated responses that require the presence of a complex regulatory system.

Zonula occludens toxin, which is produced by *Vibrio cholerae*, has been characterized by Fasano et al., in *Proc. Natl. Acad. Sci., USA*, 8:5242-5246 (1991) and the sequence has been determined (GenBank accession no. A43864). The ZOT protein of *Vibrio cholerae* phage CXTΦ exploits the physiological mechanisms of tight junction regulation. ZOT possesses multiple domains that allow a dual function of the protein as a morphogenetic phage peptide for the *Vibrio cholerae* phage CTXΦ and as an enterotoxin that modulates intestinal tight junctions. When tested on rabbit ileal mucosa, zonulin occludens toxin (ZOT) increased the intestinal permeability by modulating the structure of intercellular tight junctions.

It has been found that ZOT is capable of reversibly opening tight junctions in the intestinal mucosa, and thus ZOT, when co-administered with a therapeutic agent, is able to effect intestinal delivery of the therapeutic agent, when employed in an oral dosage composition for intestinal drug delivery (WO 96/37196; and U.S. Pat. No. 5,665,389; and Fasano et al., *J. Clin. Invest.*, 99:1158-1164 (1997). In U.S. Pat. No. 5,864,014, a ZOT receptor has been identified and purified from an intestinal cell line, i.e., CaCo2 cells. Further, in U.S. Pat. No. 5,912,323, ZOT receptors from human intestinal, heart and brain tissue have been identified and purified.

ZOT mediates a cascade of intracellular events by interacting with the surface of enteric cells. ZOT binding varies within regions of the small intestine, being detectable in the jejunum and distal ileum, decreasing along the villous-crypt axis, and not being detectable in the colon. This binding distribution coincides with the regional effect of ZOT on intestinal permeability.

Mammalian proteins that are immunologically and functionally related to ZOT have been identified. In U.S. Pat. No. 5,945,510, novel mammalian proteins that are immunologically and functionally related to ZOT and also function as the physiological modulator of mammalian tight junctions, have been identified and purified. These mammalian proteins, referred to as "zonulin", function as the physiological effector of mammalian tight junctions.

Tight junction agonists (e.g., agonists of ZOT and/or zonulin) as contemplated herein have been identified that bind to ZOT receptor. These agonists rapidly open tight junctions in a reversible and reproducible manner, and thus can be used to facilitate the intestinal bioavailability of therapeutic or immunogenic agents in the same manner as ZOT is used as an intestinal delivery enhancer, as described in the following patent references: WO 05/010022, WO 96/37196; U.S. Pat. No. 5,827,534; U.S. Pat. No. 5,665,389; and U.S. Pat. No. 5,908,825.

Tight junction antagonists (e.g., antagonists of ZOT and/or zonulin) as contemplated herein have been identified that bind to ZOT receptor, yet do not function to physiologically modulate the opening of mammalian tight junctions. See, U.S. Pat. No. 6,458,925. The peptide antagonists competitively inhibit the binding of ZOT and zonulin to the ZOT receptor, thereby inhibiting the ability of ZOT and zonulin to physiologically modulate the opening of mammalian tight junctions. Inhibiting the opening of tight junctions in various anatomical barriers may be useful in the treatment of autoimmune diseases.

SUMMARY OF THE INVENTION

The present invention provides compositions comprising one or more tight junction effectors. Such compositions may comprise a core particle, a base coat over the core particle, and a delayed-release coating disposed over the base coat. In some embodiments, the base coat may comprise one or more tight junction antagonists and/or one or more tight junction agonists. In some embodiments, the delayed-release coating may be substantially stable in gastric fluid. In a specific embodiments, the base coat may comprise one or more tight junction antagonists, one or more tight junction agonists, or combinations of one or more tight junction antagonists and tight junction agonists. In some embodiments, the delayed-release coating may comprise a Eudragit L compound.

Typically, the delayed-release coating comprises an enteric agent that is substantially stable in an acidic environment and substantially unstable in a near neutral to alkaline environment. Suitable delayed-release coatings may comprise one or more triglycerides which may be selected from the group consisting of tristearin, triolein, tricaprylin, tricaprin, trimyristin, tripalmitin and trilaurin, and a coating support agent.

An example of a tight junction agonist is zonula occludens toxin (ZOT), which is produced by *Vibrio cholerae*. A ZOT receptor agonist is a compound which is believed to mediate tight junction opening through the same receptor utilized by ZOT. In another embodiment, a tight junction agonist may comprise zonulin. A zonulin receptor agonist is a compound which is believed to mediate tight junction opening through the same receptor utilized by zonulin. Both ZOT receptor agonists and zonulin receptor agonists are examples of tight junction agonists. Without wishing to be bound by theory, it is believed that ZOT and zonulin utilize the same receptor while functioning as tight junction agonists. In a specific embodiment, compositions of the invention may comprise a tight junction antagonist comprising a peptide comprising SEQ ID NO. 1. In another specific embodiment, compositions of the invention may comprise a tight junction agonist comprising a peptide comprising SEQ ID NO. 2.

Compositions of the invention may comprise one or more therapeutic and/or immunogenic agents. When present a therapeutic and/or an immunogenic agent may be disposed in the core particle, the base coat, and/or the delayed-release coat. Typically, the therapeutic agent and/or immunogenic agent may be disposed in the base coat and/or the core particle. Examples of suitable therapeutic agents include, but are not limited to, glucose metabolism agents (e.g., insulin, repaglinide, acetohexamide, tolbutamide, chlorpropamide, tolazamide, miglitol, glimepiride, and the like), antibiotics, antineoplastics, antihypertensives, antiepileptics, central nervous system agents, and immune system suppressants.

In one embodiment, a composition of the invention may comprise a plurality of delayed-release particles present in a tablet, capsule or powder sachet.

Compositions of the invention may be used to treat a wide variety of diseases and medical conditions. In one embodiment, the present invention provides a method of treating gastrointestinal inflammation comprising orally administering to a subject in need thereof a pharmaceutical dosage form comprising a composition of the invention. In another embodiment, the present invention provides a method for treating gastrointestinal inflammation in a human who has been examined for gastrointestinal inflammation by a medical practitioner and diagnosed in need of therapy for the gastrointestinal inflammation treatment, the method comprising orally administering to the human a pharmaceutical dosage form comprising a composition of the invention. In another embodiment, the present invention provides a method for treating diabetes in a human who has been examined for diabetes by a medical practitioner and diagnosed in need of therapy for the diabetes, the method comprising orally administering to the human a pharmaceutical dosage form comprising a composition of the invention comprising a tight junction agonist (e.g., a zonulin agonist) and insulin.

In another embodiment, the invention provides a composition comprising more that one delayed-release coated particle. Such particles may be the same or different, for example, may comprise one or more of the same or different tight junction effectors, therapeutic agents and/or immunogenic agents, and delayed-release coatings. An example of such a composition might include a first core particle, a first base coat over the first core particle, wherein the first base coat comprises one or more tight junction effectors, a first delayed-release coating disposed over the first base coat forming a first delayed-release particle, wherein the first delayed-release coating is substantially stable in gastric fluid; and a second core particle, a second base coat over the second core particle, wherein the second base coat comprises one or more tight junction effectors, and a second delayed-release coating disposed over the second base coat forming a second delayed-release particle, wherein the second delayed-release coating is substantially stable in gastric fluid. In some embodiments, the first delayed-release coating and the second delayed-release coating delay release for different times. For example, about half of the tight junction effector present in the first delayed-release particle may be released after exposure to intestinal fluid for about 5 minutes to about 10 minutes, and about half of the tight junction effector present in the second delayed-release particle may be released after exposure to intestinal fluid for about 12 minutes to about 18 minutes. In compositions of this type, tight junction effectors may be distributed in any fashion, for example, the tight junction effector present in the first delayed-release particle may comprise from about 60% to about 90% by weight of the total tight junction effector in the composition, and the tight junction effector present in the second delayed-release particle may comprise from about 10% to about 40% by weight of the total amount of the tight junction effector in the composition. Likewise a first delayed-release particle may comprises a tight junction antagonist and/or a tight junction agonist while a second delayed-release particle may comprises a tight junction antagonist and/or a tight junction agonist. Suitable tight junction antagonists for compositions of this type include, but are not limited to, tight junction antagonists comprising SEQ ID NO: 1. Suitable tight junction agonists for compositions of this type include, but are not limited to, tight junction agonists comprising SEQ ID NO:2. Compositions of this type may further comprise one or more therapeutic agents and/or immunogenic agents disposed in any fashion. For example, a first delayed-release particle and/or a second delayed-release particle may comprise one or more therapeutic agents and/or one or more immunogenic agents. Compositions of this type may comprise a plurality of first delayed-release particles and/or second delayed-release particles. Compositions of this type may be used to treat a variety of diseases and/or medical conditions, for example, the invention provides a method of treating gastrointestinal inflammation comprising orally administering to a patient in need thereof the composition comprising a first delayed-release particle and a second delayed-release particle.

In one specific embodiment, the invention provides a composition comprising a core particle, a base coat over the core particle, wherein the base coat comprises a tight junction antagonist comprising SEQ ID: 1 and a delayed-release coating disposed over the base coat, wherein the delayed-release coating is substantially stable in gastric fluid. A suitable core particle for such a composition may be from about 25 to about 30 mesh in size. The base coat may comprise a binder (e.g., Baker's sugar) and the delayed-release coating may comprise Eudragit L30D. Any amount of one or more tight junction antagonists may be used for example, one or more tight junction antagonists may make up about 0.1 wt % to about 20 wt % of the composition, about 1 to about 20 wt % of the composition, about 1 wt % to about 10 wt % of the composition, or about 4 to about 6 wt % of the composition.

In another specific embodiment, the invention provides a composition comprising a core particle, a base coat over the core particle, wherein the base coat comprises a tight junction agonist comprising SEQ ID:2, and a delayed-release coating disposed over the base coat, wherein the delayed-release coating is substantially stable in gastric fluid. A suitable core particle for such a composition may be from about 25 to about 30 mesh in size. The base coat may comprise a binder (e.g., Baker's sugar) and the delayed-release coating may comprise Eudragit L30D. Any amount of one or more tight junction agonists may be used for example, one or more tight junction agonists may make up about 0.1 wt % to about 20 wt % of the composition, about 1 to about 20 wt % of the composition, about 1 wt % to about 10 wt % of the composition, or about 4 to about 6 wt % of the composition. Such compositions may further comprise one or more therapeutic agents and/or one or more immunogenic agents. Suitable therapeutic agents include, but are not limited to, glucose metabolism agents (e.g., insulin, repaglinide, acetohexamide, tolbutamide, chlorpropamide, tolazamide, miglitol, glimepiride, and the like), antibiotics, antineoplastics, antihypertensives, antiepileptics, central nervous system agents, and immune system suppressants. Suitable immunogenic agents include, but are not limited to, vaccines (e.g., peptide vaccines, attenuated microorganism vaccines, and/or attenuated virus vaccines).

BRIEF DESCRIPTION OF THE DRAWINGS

FIG. 1 is a graph of the percentage of tight junction effector released as function of time in pH 6 dissolution media dissolution from a two bead formulation prepared in accordance with one embodiment of the invention.

DESCRIPTION OF THE INVENTION

The invention is directed to compositions comprising one or more tight junction agonists and/or tight junction antagonists. As used herein, "tight junction effector" may be used to refer collectively to tight junction agonists and tight junction antagonists. The term "antagonist" is defined as a compound that prevents, inhibits, reduces or reverses the response triggered by an agonist. Thus, a tight junction agonist as used herein is a compound that mediates the opening of tight junctions (e.g., agents that induce physiological, transient disassembly of tight junctions); a tight junction antagonist is a compound that prevents, inhibits, reduces or reverses the opening or a tight junction mediated by a tight junction agonist (e.g., agents that prevent physiological, transient disassembly of tight junctions). In some embodiments, a tight junction agonist may operate by binding to the ZOT and/or zonulin receptor, i.e., may be a ZOT and/or zonulin receptor agonist. In some embodiments, a tight junction antagonist may operate by binding to the ZOT and/or zonulin receptor, i.e., may be a ZOT and/or zonulin receptor antagonist. Without wishing to be bound by theory, it is believed that ZOT and zonulin modulate tight junction opening through the same receptor. In some embodiments, tight junction agonist would not include agents that physically disrupt the tight junction structure, for example, detergents. In some embodiments, a tight junction antagonist would not include compounds that function by binding to a tight junction agonist directly. Examples of suitable tight junction effectors include, but are not limited to, peptides comprising one or more of the following sequences:

GGVLVQPG (SEQ. ID NO: 1, a tight junction antagonist sometimes referred to as Larazotide acetate (AT1001)) and FCIGRL (SEQ ID NO: 2, a tight junction agonist) and functional derivatives of these sequences.

For example, functional derivatives of peptide GGVLVQPG include, but are not limited to, Gly Arg Val Cys Val Gln Pro Gly, (SEQ ID NO: 3)

Gly Arg Val Cys Val Gln Asp Gly, (SEQ ID NO: 4)

Gly Arg Val Leu Val Gln Pro Gly, (SEQ ID NO: 5)

Gly Arg Val Leu Val Gln Asp Gly, (SEQ ID NO: 6)

Gly Arg Leu Cys Val Gln Pro Gly, (SEQ ID NO: 7)

Gly Arg Leu Cys Val Gln Asp Gly, (SEQ ID NO: 8)

Gly Arg Leu Leu Val Gln Pro Gly, (SEQ ID NO: 9)

Gly Arg Leu Leu Val Gln Asp Gly, (SEQ ID NO: 10)

Gly Arg Gly Cys Val Gln Pro Gly, (SEQ ID NO: 11)

Gly Arg Gly Cys Val Gln Asp Gly, (SEQ ID NO: 12)

Gly Arg Gly Leu Val Gln Pro Gly, (SEQ ID NO: 13)

Gly Arg Gly Leu Val Gln Asp Gly, (SEQ ID NO: 14)

Gly Gly Val Cys Val Gln Pro Gly, (SEQ ID NO: 15)

Gly Gly Val Cys Val Gln Asp Gly, (SEQ ID NO: 16)

Gly Gly Val Leu Val Gln Asp Gly, (SEQ ID NO: 17)

Gly Gly Leu Cys Val Gln Pro Gly, (SEQ ID NO: 18)

Gly Gly Leu Cys Val Gln Asp Gly, (SEQ ID NO: 19)

Gly Gly Leu Leu Val Gln Pro Gly, (SEQ ID NO: 20)

Gly Gly Leu Leu Val Gln Asp Gly, (SEQ ID NO: 21)

Gly Gly Gly Cys Val Gln Pro Gly, (SEQ ID NO: 22)

Gly Gly Gly Cys Val Gln Asp Gly, (SEQ ID NO: 23)

Gly Gly Gly Leu Val Gln Pro Gly, (SEQ ID NO: 24)

Gly Gly Gly Leu Val Gln Asp Gly, (SEQ ID NO: 25)
and

Val Asp Gly Phe Gly Arg Ile Gly. (SEQ ID NO: 26)

For example, functional derivatives of peptide FCIGRL include, but are not limited to, Xaa$_1$ Cys Ile Gly Arg Leu, (SEQ ID NO: 27)

Phe Xaa$_2$ Ile Gly Arg Leu, (SEQ ID NO: 28)

Phe Cys Xaa$_3$ Gly Arg Leu, (SEQ ID NO: 29)

Phe Cys Ile Xaa$_4$ Arg Leu, (SEQ ID NO: 30)

Phe Cys Ile Gly Xaa$_5$ Leu, (SEQ ID NO: 31)
and

Phe Cys Ile Gly Arg Xaa$_6$. (SEQ ID NO: 32)

Xaa$_1$ may be selected from the group consisting of Ala, Val, Leu, Ile, Pro, Trp, Tyr, and Met; Xaa$_2$ may be selected from the group consisting of Gly, Ser, Thr, Tyr, Asn, and Gln; Xaa$_3$ may be selected from the group consisting of Ala, Val, Leu, Ile, Pro, Trp, and Met; Xaa$_4$ may be selected from the group consisting of Gly, Ser, Thr, Tyr, Asn, Ala, and Gln; Xaa$_5$ may be selected from the group consisting of Lys and His; and Xaa$_6$ may be selected from the group consisting of Ala, Val, Leu, Ile, Pro, Trp, and Met.

Further functional derivatives of (SEQ ID NO:2) include:

Xaa$_1$ Xaa$_2$ Ile Gly Arg Leu, (SEQ ID NO: 33)

Xaa$_1$ Cys Xaa$_3$ Gly Arg Leu, (SEQ ID NO: 34)

Xaa$_1$ Cys Ile Xaa$_4$ Arg Leu, (SEQ ID NO: 35)

Xaa$_1$ Cys Ile Gly Xaa$_5$ Leu, (SEQ ID NO: 36)

Xaa$_1$ Cys Ile Gly Arg Xaa$_6$, (SEQ ID NO: 37)

```
Phe Xaa₂ Xaa₃ Gly Arg Leu,          (SEQ ID NO: 38)

Phe Xaa₂ Ile Xaa₄ Arg Leu,          (SEQ ID NO: 39)

Phe Xaa₂ Ile Gly Xaa₅ Leu,          (SEQ ID NO: 40)

Phe Xaa₂ Ile Gly Arg Xaa₆,          (SEQ ID NO: 41)

Phe Cys Xaa₃ Xaa₄ Arg Leu,          (SEQ ID NO: 42)

Phe Cys Xaa₃ Gly Xaa₅ Leu,          (SEQ ID NO: 43)

Phe Cys Xaa₃ Gly Arg Xaa₆,          (SEQ ID NO: 44)

Phe Cys Ile Xaa₄ Xaa₅ Leu,          (SEQ ID NO: 45)

Phe Cys Ile Xaa₄ Arg Xaa₆,          (SEQ ID NO: 46)
and

Phe Cys Ile Gly Xaa₅ Xaa₆.          (SEQ ID NO: 47)
```

$Xaa_1$ may be selected from the group consisting of Ala, Val, Leu, Ile, Pro, Trp, Tyr, and Met; $Xaa_2$ is selected from the group consisting of Gly, Ser, Thr, Tyr, Asn, and Gln; $Xaa_3$ is selected from the group consisting of Ala, Val, Leu, Ile, Pro, Trp, and Met; $Xaa_4$ is selected from the group consisting of Gly, Ser, Thr, Tyr, Asn, Ala, and Gln; $Xaa_5$ is selected from the group consisting of Lys and His; $Xaa_6$ is selected from the group consisting of Ala, Val, Leu, Ile, Pro, Trp, and Met.

Also contemplated are compositions comprising tight junction effectors typically classified by one of ordinary skill as small molecules, peptides, peptide mimetics and peptide analogues based on the peptides of SEQ ID Nos. 1-47. When the tight junction effector is a peptide, any length of peptide may be used. For example, an effector may be about 3, about 4, about 5, about 6, about 7, about 8, about 9, about 10, about 11, about 12, about 13, about 14 or about 15 amino acids in length.

In some embodiments, when the effector is a peptide tight junction agonist, the peptide may be from about 3 to about 12, from about 4 to about 12, from about 5 to about 12, from about 6 to about 12, from about 7 to about 12, from about 8 to about 12, from about 9 to about 12, from about 10 to about 12, from about 3 to about 10, from about 4 to about 10, from about 5 to about 10, from about 6 to about 10, from about 7 to about 10, from about 8 to about 10, from about 9 to about 10 amino acids in length. In some embodiments, when the tight junction effector is a tight junction agonist peptide, the peptide may be 9 amino acids or less in length.

In some embodiments, when the effector is a peptide tight junction antagonist, the peptide may be from about 3 to about 25, from about 6 to about 25, from about 8 to about 25, from about 10 to about 25, from about 15 to about 25, from about 20 to about 25, from about 6 to about 20, from about 8 to about 20, from about 10 to about 20, from about 15 to about 20, from about 6 to about 15, from about 8 to about 15, from about 10 to about 15, from about 6 to about 10, from about 8 to about 10, or from about 9 to about 10 amino acids in length. In some embodiments, a peptide antagonist may be 10 amino acids or less in length.

The compositions of the invention may be formulated for enteric delivery, for example, may comprise one or more coatings, for example, delayed-release coating containing one or more enteric agents. A delayed-release coating is typically substantially stable in gastric fluid and substantially unstable (e.g., dissolves rapidly or is physically unstable) in intestinal fluid, thus providing for substantial release of the tight junction effector from the composition in the duodenum or the jejunum. The invention also contemplates that the composition may optionally include one or more therapeutic or immunogenically active molecules.

Compositions of the invention may comprise one or more tight junction effectors at a level of from about 0.1 wt % to about 20 wt %, from about 0.1 wt % to about 18 wt %, from about 0.1 wt % to about 16 wt %, from about 0.1 wt % to about 14 wt %, from about 0.1 wt % to about 12 wt %, from about 0.1 wt % to about 10 wt %, from about 0.1 wt % to about 8 wt %, from about 0.1 wt % to about 6 wt %, from about 0.1 wt % to about 4 wt %, from about 0.1 wt % to about 2 wt %, from about 0.1 wt % to about 1 wt %, from about 0.1 wt % to about 0.9 wt %, from about 0.1 wt % to about 0.8 wt %, from about 0.1 wt % to about 0.7 wt %, from about 0.1 wt % to about 0.6 wt %, from about 0.1 wt % to about 0.5 wt %, from about 0.1 wt % to about 0.4 wt %, from about 0.1 wt % to about 0.3 wt %, or from about 0.1 wt % to about 0.2 wt % of the total weight of the composition. Compositions of the invention may comprise one or more tight junction effectors at a level of about 0.1 wt %, about 0.2 wt %, about 0.3 wt %, about 0.4 wt %, about 0.5 wt %, about 0.6 wt %, about 0.7 wt %, about 0.8 wt %, or about 0.9 wt % based on the total weight of the composition.

Compositions of the invention may comprise one or more tight junction effectors at a level of from about 1 wt % to about 20 wt %, from about 1 wt % to about 18 wt %, from about 1 wt % to about 16 wt %, from about 1 wt % to about 14 wt %, from about 1 wt % to about 12 wt %, from about 1 wt % to about 10 wt %, from about 1 wt % to about 9 wt %, from about 1 wt % to about 8 wt %, from about 1 wt % to about 7 wt %, from about 1 wt % to about 6 wt %, from about 1 wt % to about 5 wt %, from about 1 wt % to about 4 wt %, from about 1 wt % to about 3 wt %, or from about 1 wt % to about 2 wt % of the total weight of the composition. Compositions of the invention may comprise one or more tight junction effectors at a level of about 1 wt %, about 2 wt %, about 3 wt %, about 4 wt %, about 5 wt %, about 6 wt %, about 7 wt %, about 8 wt %, or about 9 wt % based on the total weight of the composition.

The terms "stable in gastric fluid" or "stable in acidic environments" refers to a composition that releases 30% or less by weight of the total tight junction antagonist or agonist in the composition in gastric fluid with a pH of 5 or less, or simulated gastric fluid with a pH of 5 or less, in approximately sixty minutes. Compositions of the of the invention may release from about 0% to about 30%, from about 0% to about 25%, from about 0% to about 20%, from about 0% to about 15%, from about 0% to about 10%, 5% to about 30%, from about 5% to about 25%, from about 5% to about 20%, from about 5% to about 15%, from about 5% to about 10% by weight of the total tight junction antagonist or agonist in the composition in gastric fluid with a pH of 5, or less or simulated gastric fluid with a pH of 5 or less, in approximately sixty minutes. As use herein, "about" used to modify a numerical value means within 10% of the value. Compositions of the invention may release about 1%, about 2%, about 3%, about 4%, about 5%, about 6%, about 7%, about 8%, about 9%, or about 10% by weight of the total tight junction antagonist or agonist in the composition in gastric fluid with a pH of 5 or less, or simulated gastric fluid with a pH of 5 or less, in approximately sixty minutes.

The term "unstable in intestinal fluid" refers to a composition that releases 70% or more by weight of the total tight junction effector in the composition in intestinal fluid or simulated intestinal fluid in approximately sixty minutes. The term "unstable in near neutral to alkaline environments" refers to a composition that releases 70% or more by weight of the total amount of tight junction agonist or antagonist in the composition in intestinal fluid with a pH of 5 or greater, or simulated intestinal fluid with a pH of 5 or greater, in approximately ninety minutes. For example, a composition that is unstable in near neutral or alkaline environments may release 70% or more by weight of a tight junction agonist peptide or a tight junction antagonist peptide in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

In one embodiment, the delayed-release coating may remain essentially intact, or may be essentially insoluble, in gastric fluid. The stability of the delayed-release coating can be pH dependent. Delayed-release coatings that are pH dependent will be substantially stable in acidic environments (pH 5 or less), and substantially unstable in near neutral to alkaline environments (pH greater than 5). For example, the delayed-release coating may essentially disintegrate or dissolve in near neutral to alkaline environments such as are found in the small intestine.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

Alternatively, the stability of the delayed-release coating can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans.

As used herein, tight junction antagonists prevent, inhibit or reduce the opening of tight junctions. Tight junction agonists mediate or facilitate or augment the opening of tight junctions. Tight junction antagonists may inhibit the binding of a tight junction agonist (e.g., ZOT and zonulin) to one or more receptor molecules (e.g., the ZOT receptor), thereby inhibiting or reducing the ability of the agonist to physiologically modulate the opening of the tight junctions.

A target organ for the release of the tight junction agonists or tight junction antagonists from the compositions of the invention is the small intestine, particularly the duodenum and the jejunum. U.S. Pat. Nos. 6,458,925, 5,945,510 and 5,827,534 discuss the possibility of oral dosage compositions for small intestinal delivery of tight junction antagonists, zonulin or ZOT via gastroresistent tablets or capsules as described in the art. See Remington's Pharmaceutical Sciences, 16th Ed., Eds. Osol, Mack Publishing Co., Chapter 89 (1980); Digenis et al, *J. Pharm. Sci.*, 83:915-921 (1994); Vantini et al, *Clinica Terapeutica*, 145:445-451 (1993); Yoshitomi et al, Chem. Pharm. Bull., 40:1902-1905 (1992); Thoma et al, *Pharmazie,* 46:331-336(1991); Morishita et al, *Drug Design and Delivery,* 7:309-319 (1991); and Lin et al, *Pharmaceutical Res.,* 8:919-924 (1991) for examples of the preparation of such tablets or capsules.

In one embodiment, enteric formulations of the invention may utilize one or more delayed-release coatings and an inert core to provide for effective, delayed yet substantial delivery of the tight junction agonist or antagonist compounds together with, optionally, other therapeutic and/or immunogenic agents. The coated compositions are substantially stable in acidic environments or gastric fluid, and substantially unstable in near neutral to alkaline or intestinal fluid. Compositions of the invention may also include additional compounds, such as buffers, excipients, talc or binding agents, within the spirit of the invention.

Particles Comprising a Tight Junction Agonist or Antagonist and an Enteric Coating In one embodiment, the invention provides a composition comprising: a core particle having a base coat comprising one or more tight junction agonists and/or one or more tight junction antagonists, and a delayed-release coating disposed over the coated core particle. The delayed-release coating may be substantially stable in acidic environments and/or gastric fluid, and/or substantially unstable in near neutral to alkaline environments or intestinal fluid thereby exposing the coated core particle to intestinal fluid. The base coat comprising one or more tight junction agonists and/or one or more tight junction antagonists may further comprise one or more therapeutic agents. Optionally a plurality of base coats may be applied to the core each of which may contain a tight junction effector and/or a therapeutic agent. Optionally, the core particle may comprise one or more tight junction effectors and/or one or more therapeutic agents.

In one embodiment, a subject in need of treatment may be provided with a composition as described above in the form of a tablet or capsule that contains the coated core particles. Such tablets or capsules may be orally administered. Alternatively, the subject can be provided with a powder sachet comprising the coated core particles and, optionally, one or more adjuvants such as a sweetener or flavoring agent. The subject may then mix the powder with a liquid and orally administer the mixture.

The core particles can include spheres or seeds having an average size of from about 5 to about 50 mesh, from about 5 to about 45 mesh, from about 5 to about 40 mesh, from about 5 to about 35 mesh, from about 5 to about 30 mesh, from about 5 to about 25 mesh, from about 5 to about 20 mesh, from about 5 to about 15 mesh, from about 5 to about 10 mesh, from about 10 to about 50 mesh, from about 10 to about 45 mesh, from about 10 to about 40 mesh, from about 10 to about 35 mesh, from about 10 to about 30 mesh, from about 10 to about 25 mesh, from about 10 to about 20 mesh, from about 10 to about 15 mesh, from about 15 to about 50 mesh, from about 15 to about 45 mesh, from about 15 to about 40 mesh, from about 15 to about 35 mesh, from about 15 to about 30 mesh, from about 15 to about 25 mesh, from about 15 to about 20 mesh, from about 20 to about 50 mesh, from about 20 to about 45 mesh, from about 20 to about 40 mesh, from about 20 to about 35 mesh, from about 20 to about 30 mesh, from about 20 to about 25 mesh, from about 25 to about 50 mesh, from about 25 to about 45 mesh, from about 25 to about 40 mesh, from about 25 to about 35 mesh, from about 25 to about 30 mesh, from about 30 to about 50 mesh, from about 30 to about 45 mesh, from about 30 to about 40 mesh, or from about 30 to about 35 mesh. Core particles may be coated with a coating composition, which may include one or more tight junction agonists and/or one or more tight junction antagonists and/or one or more therapeutic agents as described herein.

The core particles can be water insoluble particles comprising different oxides, celluloses, organic polymers and other materials, and mixtures thereof, or water soluble particles comprising different inorganic salts, sugars, non-pareils and other materials, and mixtures thereof. The core particle may comprise from about 25 to about 75, from about 30 to about 75, from about 35 to 75, from about 40 to about 75, from about 45 to about 75, from about 50 to about 75, from about 55 to about 75 from about 60 to about 75 from about 65 to about 75, from about 70 to about 75, from about 25 to about 70, from about 25 to about 65, from about 25 to about 60, from about 25 to about 55, from about 25 to about 50 from about 25 to about 45, from about 25 to about 40, from about 25 to about 35, from about 25 to about 30, from about 30 to about 60, from about 35 to about 55, from about 40 to about 50, from about 42 to about 47, or from about 42 to about 45 wt % of the final particle composition. In one embodiment, the core particle may comprise about 43.2 wt % of the final particle composition. Common forms of such core particles are commercially available such as Celpheres™ or non-pareils. The core particles may optionally comprise one or more tight junction effector compounds and/or one or more therapeutic agents. Core particles may be coated using techniques known in the art, for example, techniques described in U.S. Pat. No. 6,248,363 (in particular the Examples) and U.S. Pat. No. 6,294,192 (in particular the examples).

Compositions of the invention can also include one or more of the following formulation aids known to those skilled in the art such as a surface active agent, a filler, a disintegrating agent, an alkaline material and/or a binder.

Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate. The surface active agent may be present at a level of from about 0.1 wt % to about 5 wt % from about 0.1 wt % to about 4.5 wt %, from about 0.1 wt % to about 4.0 wt %, from about 0.1 wt % to about 3.5 wt %, from about 0.1 wt % to about 3.0 wt %, from about 0.1 wt % to about 2.5 wt %, from about 0.1 wt % to about 2.0 wt %, from about 0.1 wt % to about 1.5 wt %, from about 0.1 wt % to about 1.0 wt %, from about 0.1 wt % to about 0.5 wt %, from about 0.5 wt % to about 5.0 wt %, from about 1.0 wt % to about 5.0 wt % from about 1.5 wt % to about 5.0 wt %, from about 2.0 wt % to about 5.0 wt %, from about 2.5 wt % to about 5.0 wt %, from about 3.0 to about 5.0 wt %, from about 3.5 wt % to about 5.0 wt %, from about 4.0 wt % to about 5.0 wt %, from about 4.5 wt % to about 5.0 wt %, from about 0.25 wt % to about 2.5 wt %, from about 1.0 wt % to about 2.0 wt %, or from about 1.5 wt % to about 2.0 wt % based on the total weight of the final particle composition. In some embodiments, surface active agents may be present in the compositions of the invention at a level of about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, or about 2.0 wt % based on the total weight of the final particle composition. In one embodiment, compositions of the invention may comprise about 1.8 wt % surfactant based on the total weight of the final particle composition.

Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition the alkaline material may be selected from the group consisting of antacid materials such as aluminum hydroxides, calcium hydroxides, magnesium hydroxides and magnesium oxide. The alkaline agent may be present at a level of from about 1 wt % to about 20 wt %, from about 1 wt % to about 18 wt %, from about 1 wt % to about 16 wt %, from about 1 wt % to about 14 wt %, from about 1 wt % to about 12 wt %, from about 1 wt % to about 10 wt %, from about 1 wt % to about 8 wt %, from about 1 wt % to about 6 wt %, from about 1 wt % to about 4 wt %, or from about 1 wt % to about 2 wt %, based on the total weight of the coating composition, depending on the relative strength of the alkaline material. In some embodiments, alkaline material may be present in the compositions of the invention at a level of about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, about 14 wt %, about 15 wt %, about 16 wt %, about 17 wt %, about 18 wt %, about 19 wt %, or about 20 wt % based on the total weight of the coating composition.

Binders suitable for use in the compositions of the invention include, but are not limited to, any pharmaceutically acceptable, non-toxic pharmaceutically acceptable binder. A binder may be a water soluble polymer. In some embodiments a binder may comprise one or more binders selected from the group consisting of polyvinyl alcohol, polyvinylpyrrolidone, methylcellulose, hydroxypropyl cellulose, hydroxymethyl cellulose and the like. When a water soluble binder is used, it may be applied from an aqueous medium such as water. Compositions of the invention may comprise one or more binders at a level of from about 1 wt % to about 15 wt % based on the total weight of the coating composition, depending on the relative strength of the alkaline material. Fillers, for example, sugars such as lactose, dextrose, sucrose and maltose, microcrystalline cellulose and the like can also be included in the coating composition. A preferred commercially available filler is Bakers Special Sugar.

Before applying the delayed-release coating to the coated core particle the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, titanium dioxide, talc and other additives can also be included in the separating layer.

In one embodiment, the delayed-release coating includes an enteric agent that is substantially stable in acidic environments and substantially unstable in near neutral to alkaline environments. A delayed-release coating composition can be dispersed or dissolved in either water or in a suitable organic solvent and applied to the core particle by methods well known to those of ordinary skill in the art. One or more delayed-release coatings can be applied to the coated core particle. Also, as described, an optional separating layer can be applied to the coated core particles prior to the application of the delayed-release coating.

The enteric agent can be selected from the group consisting of, e.g., solutions or dispersions of methacrylic acid copolymers, cellulose acetate phthalate, hydroxypropylmethyl cellulose phthalate, polyvinyl acetate phthalate, carboxymethylethylcellulose, and Eudragit-type polymer (poly (methacrylic acid, methylmethacrylate), hydroxypropyl methylcellulose acetate succinate, cellulose acetate trimellitate, shellac or other suitable enteric coating polymers. The Eudragit-type polymer include Eudragit L, NE, RL, RS. Eudragit L polymers are preferred. The enteric agent may be a combination of the foregoing solutions or dispersions.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare sustained release formulations. Suitable water insoluble polymers include pharmaceutically acceptable non-toxic polymers that are substantially insoluble in aqueous media, e.g. water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE®. Insoluble polymers useful in the present invention include polyvinyl esters, polyvinyl acetals, polyacrylic acid esters, butadiene styrene copolymers, and the like.

In another embodiment, the delayed-release coating contains an enteric agent that is substantially stable in gastric fluid. The enteric agent will be sensitive to pancreatic lipase. The enteric agents sensitive to pancreatic lipase include the triglycerides, tristearin, triolein, tricaprylin, tricaprin, trimyristin, tripalmitin and trilaurin. One or more of these triglycerides in combination with a coating support agent, e.g., a cellulose-type material such as ethylcellulose, are used to prepare a delayed relay coating composition, which is then applied to the coated core particles.

A delayed-release coating composition may comprise from 0.1 wt % to 5 wt % of a triglyceride or a mixture of triglycerides, and 0.5 wt % to 10 wt % of a coating support agent. Another delayed-release coating composition will comprise from 0.5 wt % to 3 wt % of a triglyceride or a mixture of triglycerides, and 1 wt % to 5 wt % of a coating support agent.

One or more delayed-release coatings can be applied to the coated core particle. For example, an additional delayed-release coatings can be applied to the coated core particle in addition to an enteric agent sensitive to pancreatic lipase. Such an additional coating can include an enteric agent that is substantially stable in an acidic environment as described herein. Also, as described, an optional separating layer can be applied to the coated core particles prior to the application of the delayed-release coating.

The delayed-release coating compositions can also include one or more inert processing aids in an amount from 10 to 80 wt % based on the total weight of the coating composition. The inert processing aids include finely divided forms of talc, silicon dioxide, magnesium stearate and the like.

The delayed-release coating compositions can also contain pharmaceutically acceptable plasticizers to obtain the desired mechanical properties such as flexibility and hardness. Such plasticizers include, but are not limited to, triacetin, citric acid esters, phthalic acid esters, dibutyl sebacate, cetyl alcohol, polyethylene glycols, polysorbates or other plasticizers.

The amount of plasticizer is optimized for each delayed-release coating in relation to the selected enteric agent used. A selected plasticizer and the applied amount of enteric agent are optimized for the desired mechanical properties, i.e., flexibility and hardness of the delayed-release coating. The hardness of the delayed-release coating is often exemplified as Vickers hardness, and is adjusted so that the acid resistance of the final coated particle does not decrease significantly during the compression of the particles into tablets. Other compounds can be added to the delayed-release coating composition to increase film thickness and to increase the resistance to acidic gastric juices in the stomach.

The delayed-release coating compositions can also include one or more application solvents. Some of the more common solvents that can be used to apply the delayed-release coating composition include isopropyl alcohol, acetone, methylene chloride and the like. Generally the enteric agent and inert processing aids will account for 5 wt % to 60 wt % of coating composition including the weight of the solvent.

The coated particle with the delayed-release coating can further be covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

It is understood that the overall release profile of the final product may be adjusted by combining two or more particle types with different release profiles. For example, in one embodiment, about half of the coated core particles are a first coated core particle type that has an enteric coating that exposes the tight junction agonist or antagonist to intestinal fluid after about 5 minutes to about 10 minutes, and about half of the coated core particles are a second coated core particle type that has an enteric coating that exposes the tight junction agonist or antagonist to intestinal fluid after about 12 minutes to about 18 to 60 minutes. In another embodiment, the first coated particles comprise from 60% to 90% by weight, and the second coated particles comprise 10% to 40% by weight, of the total amount of the tight junction effector in the composition.

Compositions Comprising One or More Tight Junction Antagonists

In on embodiment, compositions of the invention may comprise one or more tight junction antagonists. An example of suitable antagonists of zonulin are peptide GGVLVQPG (SEQ ID NO: 1) and derivatives thereof, particularly derivatives having one or more conservative amino acid substitutions. Such compositions may be used to treat a wide variety of diseases including, but not limited to, autoimmune diseases. Examples of autoimmune diseases that can be treated using the compositions of the invention include, but are not limited to, celiac disease, primary biliary cirrhosis, IgA nephropathy, Wegener's granulomatosis, multiple sclerosis, scleroderma, systemic sclerosis, type 1 diabetes mellitus, rheumatoid arthritis, Crohn's disease, lupus erythematosus, Hashimoto's thyroiditis (underactive thyroid), Graves' disease (overactive thyroid), autoimmune hepatitis, autoimmune inner ear disease, bullous pemphigoid, Devic's syndrome, Goodpasture's syndrome, Lambert-Eaton myasthenic syndrome (LEMS), autoimmune lymphproliferative syndrome (ALPS), paraneoplastic syndromes, polyglandular autoimmune syndromes (PGA), and alopecia areata.

Compositions of the invention can be used as anti-inflammatory agents for the treatment of gastrointestinal inflammation that gives rise to increased intestinal permeability. Thus, the antagonists are useful, e.g., in the treatment of intestinal conditions that cause protein losing enteropathy. Protein losing enteropathy may arise due to:

infection, e.g., *C. difficile* infection, enterocolitis, shigellosis, viral gastroenteritis, parasite infestation, bacterial overgrowth, Whipple's disease;

diseases with mucosal erosion or ulcerations, e.g., gastritis, gastric cancer, collagenous colitis, inflammatory bowel disease; and mucosal diseases without ulceration, e.g., Menetrier's disease, celiac disease, eosinophilic gastroenteritis.

Other diseases that may be treated with the compositions and methods of the invention include, but are not limited to, diseases marked by lymphatic obstruction, e.g., congenital intestinal lymphangiectasia, sarcoidosis lymphoma, mesenteric tuberculosis, and after surgical correction of congenital heart disease; and immune diseases, e.g., systemic lupus erythematosus or food allergies, primarily to milk (see also Table 40-2 of Pediatric Gastrointestinal Disease Pathophysiology Diagnosis Management, Eds. Wyllie et al, Saunders Co. (1993), pages 536-543; which is incorporated by reference herein in its entirety).

The pharmaceutically effective amount of an antagonist of zonulin will vary depending upon the disease or condition being treated, as well as the age, weight and sex of the subject being treated. Generally, the amount of antagonist used to inhibit gastrointestinal inflammation, e.g., to inhibit zonulin biological activity, is in the range of about 1.0 μg to 1000 μg, preferably about 1.0 μg to 100 μg.

The peptide tight junction antagonists can be chemically synthesized and purified using well-known techniques, such as described in High Performance Liquid Chromatography of Peptides and Proteins: Separation Analysis and Conformation, Eds. Mant et al, C.R.C. Press (1991), and a peptide synthesizer, such as Symphony (Protein Technologies, Inc); or by using recombinant DNA techniques, i.e., where the nucleotide sequence encoding the peptide is inserted in an appropriate expression vector, e.g., an *E. coli* or yeast expression vector, expressed in the respective host cell, and then purified using well-known techniques.

Compositions Comprising One or More Tight Junction Agonists

In one embodiment, a tight junction agonist may comprise a peptide sequence. Examples of suitable peptide sequences are FCIGRL (SEQ ID NO: 2) and derivatives thereof, particularly derivatives having one or more conservative amino acid substitutions. A peptide sequence may be used alone or may be part of a larger molecule, e.g., a polypeptide. When an agonist of zonulin comprises a polypeptide, such a polypeptide is typically less than 100 amino acid residues in length, or less than 50, 40, 30, 20, 10, or 8 amino acid residues. The polypeptide may contain only the six amino acids FCIGRL (SEQ ID NO: 2), or it can include additional amino acids. The other amino acids may provide other functions, e.g., antigen tags, for facilitating purification.

In one embodiment, compositions of the invention may comprise one or more tight junction agonists and one or more therapeutic and/or immunogenic agents. In one embodiment, a composition of the invention may comprise a therapeutic and/or an immunogenic agent for treating, ameliorating or preventing one or more diseases and an agonist of a human receptor of zonulin and *vibrio cholerae* phage CTXΦ ZOT protein. It is also contemplated that the composition can exist in the form of a pharmaceutical kit in which the agonist and therapeutic agent are associatively packaged for simultaneous, nearly simultaneous or subsequent administration. In the later instance, the agonist and therapeutic agent are administered within 12, 8, 4, 2, or 1 hours of each other or as little as within 5, 10 or 15 minutes of each other.

Therapeutic agents that can be used in the compositions include agents that act on any organ of the body, such as heart, brain, intestine, or kidneys.

The particular therapeutic or immunogenic agent used in the composition can be, any small molecule compound, biologically active peptide, vaccine, or any other moiety otherwise not adequately absorbed through the transcellular pathway, regardless of size or charge.

Examples of drug compounds which can be employed in the present invention include, but are not limited to, drugs which act on the cardiovascular system, drugs which act on the central nervous system, antineoplastic drugs and antibiotics. Examples of drugs which act on the cardiovascular system include, but are not limited to, antihypertensives, statins, adenosine, dobutamine, dopamine, epinephrine, norepinephrine, and phentolamine. Others as are known in the art can also be used.

Examples of drugs which act on the central nervous system include, but are not limited to, doxapram, alfentanil, dezocin, nalbuphine, buprenorphine, naloxone, ketorolac, midazolam, and propofol. Other examples include, but are not limited to, antipsychotics, antidepressants, antiepileptics, and drugs used to treat Alzheimers disease. Others as are known in the art can also be used.

Examples of antineopiastic drugs include, but are not limited to, cytarabine, mitomycin, doxorubicin, vincristine and vinblastine, carboplatin, cisplatin, oxaloplatin, vinorelbine, docetaxel, paclitaxel, taxane, 5-fluorouridine related drugs, xeloda, germcitabine, and anthracline. Additional examples include, but are not limited to, Erbitux, Herceptin®, Avastin™, and estrogen receptor antagonists and agonists. Others as are known in the art can also be used.

Examples of antibiotics include, but are not limited to, methicillin, mezlocillin, piperacillin, cetoxitin, cefonicid, cefinetazole and aztreonam. Others as are known in the art can also be used.

Any type of therapeutic and/or immunogenic agent can be used in the practice of the invention. Examples of specific types of agents include, but are not limited to, RNAi, treatment aptamers, antivirals (e.g., amantadine, rimantadine, zanamavir and oseltamivir), immune suppressants (e.g., cyclosporine A), HIV fusion inhibitors (e.g., enfuvirtide), and HIV protease inhibitors, (e.g., ritonavir, saquinavir, indinavir, amprenavir, nelfinavir, lopinavir, atazanavir, entricitabine, and fosamprenavir calcium).

Examples of biologically active peptides include hormones, lymphokines, globulins, and albumins. Examples of hormones which can be employed in the present invention include testosterone, nandrolene, menotropins, insulin, growth hormone, parathyroid hormone (PTH) and urofolltropin. Others as are known in the art can also be used. If the biologically active ingredient is insulin, the oral dosage composition is useful for the treatment of diabetes. Examples of lymphokines which can be employed in the present invention include interferon-α, interferon-β, interferon-γ, interleukin-1, interleukin-2, interleukin-4 and interleukin-8.

Examples of globulins include α-globulins, β-globulins and γ-globulins (immunoglobulin). Examples of immunoglobulins which can be employed in the present invention include polyvalent IgG or specific IgG, IgA and IgM, e.g., anti-tetanus antibodies. An example of albumin which can be used is human serum albumin. Others as are known in the art can also be used.

Examples of vaccines that can be used in the compositions include peptides and attenuated microorganisms and viruses. Examples of peptide antigens include the B subunit of the heat labile enterotoxin of enterotoxigenic *E. coli*, the B subunit of cholera toxin, capsular antigens of enteric pathogens, fimbriae or pili of enteric pathogens, HIV surface antigens, dust allergens, and acari allergens. Other immunogenic compounds as are known in the art can also be used.

Examples of attenuated microorganisms and viruses that can be used in the compositions include those of enterotoxigenic *Escherichia coli*, enteropathogenic *Escherichia coif, hibrio cholerae, Shigella flexneri, Salmonella typhi* and rotavirus (Fasano et al, In: Le Vaccinazioni in Pediatria, Eds. Vierucci et al, CSH, Milan, pages 109-121 (1991); Guandalini et al, In: Management of Digestive and Liver Disorders in Infants and Children, Elsevior, Eds. Butz et al, Amsterdam, Chapter 25 (1993); Levine et al, Sem. Ped. Infect. Dis., 5.243-250 (1994); and Kaper et al, Clin. Micrbiol. Rev., 8:48-86 (1995), each of which is incorporated by reference herein in its entirety).

The pharmaceutical compositions of the invention can be used for treating, ameliorating, and/or preventing a disease. The disease can be selected from the group consisting of cancer, autoimmune, vascular, bacterial infection, gastritis, gastric cancer, collagnenous colitis, inflammatory bowel disease, osteoporosis, systemic lupus erthtematosus, food allergy, asthma, and irritable bowel syndrome.

In another embodiment, the composition can be used in a method of treating a patient with increased expression of zonulin relative to a control healthy individual. In this case, the therapeutic agent may be an antibody that was raised against amino acids SLIGKVDGTSHVTG (SEQ ID NO: 48). For example, the antibody can bind to a protein expressed in CaCo2 cells that co-localizes with a protein bound by synthetic inhibitor peptide SEQ ID NO: 1. The antibody does not bind to human or rat cells that express a recombinant human PAR-2. The antibody is not SAMl1.

It is to be understood, that for any of the antagonist and agonist peptides described in this application one or more conservative substitutions can be made in which an amino acid is exchanged for another having similar properties. Conservative substitutions of certain amino acids can be made in the agonist peptides of zonulin as well as the antagonist peptides of zonulin. For example, a conservative substitution can be made in the agonist peptide having the sequence of any one of SEQ ID NO: 1-47. Examples of conservative substitutions include, but are not limited to, Gly⇌Ala, Va⇌Ile⇌Leu, Asp⇌Glu, Lys⇌Arg, Asn⇌Gln, and Phe⇌Trp⇌Tyr. Conservative amino acid substitutions typically fall in the range of about 1 to 2 amino acid residues.

Guidance in determining which amino acid residues can be substituted without abolishing biological or immunological activity can be found using computer programs well known in the art, such as DNASTAR software, or in Dayhoff et al. (1978) in *Atlas of Protein Sequence and Structure* (Natl. Biomed. Res. Found., Washington, D.C.).

Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Particularly preferred oligopeptide analogs include substitutions that are conservative i.e., those substitutions that take place within a family of amino acids that are related in their side chains. Specifically, amino acids are generally divided into families: (1) acidic—aspartate and glutamate; (2) basic—lysine, arginine, histidine; (3) non-polar—alanine, valine, leucine, isoleucine, proline, phenylalanine, methionine, tryptopban; (4) uncharged polar—glycine, asparagine, glutamae, cysteine, serine threonine, and tyrosine; and (5) aromatic amino acids—phenylalanine, tryptophan, and tyrosine. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity.

The compositions described can be administered one to several times a day. The typical daily dose of the agonist or antagonist of zonulin varies and will depend on various factors such as the individual requirements of the patients, the mode of administration and disease. In one embodiment, antagonists of zonulin are administered prior to eating. Applications of such administrations include the treatment of Celiac disease.

In general the daily dose of the agonist or antagonist of ZOT and/or zonulin will be in the range of 1-1000 mg of active substance.

EXAMPLES

Example 1

Preparation of a Delayed-Release Particle Comprising a Tight Junction Antagonist A base coat containing the tight junction antagonist of SEQ ID NO: 1 was prepared by mixing 2000 g of water, slowly adding 15 g of the antagonist peptide. Once the peptide was dispersed, 15 g of Bakers Special Sugar was added. Total weight was adjusted to 2107 g with additional water. One skilled in the art will appreciate that binders other than Bakers Special Sugar may be used. Suitable binders are typically pharmaceutically acceptable binders including, but not limited to, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Other suitable binders include pharmaceutically acceptable binders such as polyvinyl pyrrolidone, hydroxypropyl cellulose, hydroxyethyl cellulose, ethylcellulose, polymethacrylate, waxes and the like. Mixtures of the aforementioned binders may also be used.

After complete dissolution, the base coat is applied. The quantity of base coat used is determined by the final weight of enteric-coated beads desired. For the amount described above, 3270 g of the base coat was added to a Wurster unit charged with 1000 g Non-pareils 25/30 mesh (a ratio of 3.27 g base coat/gram non-pareils) under the following conditions until coating was complete: 135-150° F., Process Air Volume (SCFM) of 10-25 adjusted to maintain fluidization; spray rate of 3-10 g/min/nozzle; and atom air pressure of 25 psi.

A delayed-release coating containing Eudragit L30D was also prepared. 15 g of Talc was added to 500 g of water and stirred vigorously for 10 minutes. 850 grams of Eudragit L30D (Type C) was sifted through a 60 mesh screen into the mixing container by vortexing without entrainment of air. 30 g of triethyl citrate Pharmaceutical Grade was then added slowly and mixed for 10 minutes under similar conditions and mixing continued until completed dissolution and dispersion occurred. Total mass was brought to 1500 g with the addition of water.

The delayed-release coating was then added to Wurster unit (containing the base coated particles) under the following conditions until coating was complete: 135-150° F., Process Air Volume (SCFM) of 10-25 adjusted to maintain fluidization; spray rate of 3-10 g/min/nozzle); and atom air pressure of 25 psi.

The final composition was as follows:

TABLE 1

| Component | wt % |
| --- | --- |
| Non-pareils 25/30 | 43.2 |
| Antagonist | 1 |
| Bakers Special Sugar | 1 |
| Talc | 0.9 |
| Ludragit L30D | 53.1 |
| Triethyl Citrate | 1.8 |

Example 2

The stability of delayed-release particles containing 4-6% tight junction antagonist peptide (SEQ ID NO: 1) was performed. Delayed-release particles prepared as described above were exposed to Simulated Gastric Fluid (SGF) containing 0.1% v/v Tween 80K under controlled temperature (37° C.±0.5° C.) and agitation in a dissolution apparatus for 1 hour. The beads were removed from the SGF and exposed to Simulated Intestinal Fluid (SIF) containing 0.1% v/v Tween 80K. Samples were pulled from the bath and analyzed by HPLC at 220 nm on a Inertsil ODS-2 HPLC Column (150 mm×3 mm, 5 µm) with an Inertsil ODS-2 HPLC Guard Column (20 mm×4.6 µm, 5 µm). Mobile Phase A: 92:8 Water: ACN, 0.1% TFA Mobile Phase B: ACN, 0.1% TFA). The chromatographic conditions are shown below.

| Time (min) | Flow rate (mL/min) | % H$_2$O 0.1% TFA | % CH3CN 0.1% TFA |
| --- | --- | --- | --- |
| 0 | 1.5 | 98 | 2 |
| 10 | 1.5 | 53.4 | 46.6 |
| 10.1 | 1.5 | 0 | 100 |
| 11.9 | 1.5 | 0 | 100 |
| 12 | 1.5 | 98 | 2 |
| 17 | | 98 | 2 |

Run time: 17 min
Detection: 220 nm
Response time: 0.5 sec
Column Temp.: 40° C. ± 1° C.
Auto Sampler Temp: 10° C. ± 2° C.
Injection Volume: 5 µl of solution The percentage of total tight junction effector released is determined by comparison to a reference standard of the effector.

Over a time course of 60 minutes, less than 8% of the antagonist peptide of SEQ ID NO: 1 was released in the presence of simulated gastric fluid (SGF) containing 0.1% v/v Tween 80K.

Simulated Gastric Fluid may be prepared as follows: per liter, place the following into a container: 2.0 gram sodium chloride, 7.0 mL concentrated hydrochloric acid, and 1.0 L water. Stir until completely dissolved. Check the pH and adjust to 1.2±0.1 with dilute HCl or NaOH. De-aerate medium. To this solution Tween 80 was added to 0.1% (v/v). Alternatively, commercially available SGF may be used (Ricca Chemical Company, Arlington, Tex.) and Tween 80K added.

Over 90% of the antagonist peptide of SEQ ID: 1 was released in the presence of simulated intestinal fluid (SIF) containing 0.1% v/v Tween 80K within 15 minutes and essentially all of the peptide was released within 60 minutes. SIF can be prepared as follows: place the following into a container: 1.9 Kg distilled water, 136 g monobasic potassium phosphate, and 18.1 gram of sodium hydroxide. Stir until completely dissolved. Dilute the solution with 18.0 Kg water. Check the pH and adjust to 6.8±0.1 with dilute HCl or NaOH. De-aerated medium. To this solution add Tween 80K to 0.1% (v/v). Alternatively, commercially available SIF may be purchase (Ricca Chemical Company, Arlington, Tex.) and Tween 80K added to 0.1% (v/v).

Example 3

Preparation of Multiparticulate Enterically Coated Bead Formulation for Delayed-Release of Tight Junction Effectors This embodiment provides for encapsulation of a combination of a plurality (e.g., 2, 3, 4, 5 etc) of different enterically coated beads. Any amount of each type of bead may be encapsulated. In some embodiments, two different beads may be encapsulated in any proportion. In one specific embodiment, almost equal proportions of two beads may be encapsulated. Each bead may be coated with any suitable coating material at any suitable coating level. In some embodiments, two beads may be coated with Eudragit L30 D55 at 20 and 70% coating levels. A formulation comprising 20% and 70% coating levels allows for the delayed-release of one or more tight junction effectors (e.g. Larazotide acetate) into both the duodenum and jejunum. For calculation of weight percentage, weight measurements are done before the two substances are put together. For example, a 70% coating level is 70 g coating polymer added to 100 g bead.

Eudragit L30D is a polymeric coating that starts to degrade at pH>5.5. Therefore beads coated with Eudragit L30D55 are designed to remain intact as they pass through the stomach but start to dissolve as soon as they enter the duodenum. This is the case for the beads coated with 20% Eudragit L30D55. Beads coated with 70% Eudragit L30D55 dissolve about 30 minutes later in pH 6.0 dissolution media and are designed to start releasing as soon as they enter the jejunum. FIG. 1 shows a dissolution profile of beads prepared according to this embodiment.

Essentially beads may be prepared in two steps. First drug is layered onto non-pareil beads. Then the drug layered beads may be enterically coated with L30D55 to the desired level.

It was found that coating less than 20% Eudragit L30D55 started to dissolve in vitro in simulated gastric fluid (pH 1.1) and therefore will not remain undissolved in the stomach. Coating more than 70% was not possible due to limitations of the coating material.

In one embodiment, beads may be polymethacrylate which is a 1:1 copolymer of methacrylic acid and ethyl acrylate (e.g., Eudragit L30 D-55).

Example 4

In some embodiments, various parameters may be modified in order to optimize Larazotide acetate enteric coated bead formulation with the goal of improving stability of the tight junction effector (both chemical and dissolution stability), for example, as measured at 40° C./75% relative humidity conditions.

In some embodiments, one or more additional coatings may be applied to the formulations of the invention. For example, one or more seal coats and/or top coats may be used. In a specific embodiment, a seal coat may be applied to the drug layer. In embodiments of this type, a core particle may be coated with tight-junction-effector-containing layer, which may be further coated with a sealing coat. After application of the sealing coat, one or more delayed-release coating (e.g., Eudragit L30D55) may be applied. After the delayed-release coating is applied, a sealing coat may be applied. Any suitable sealing coat known to those skilled in the art may be used. Examples of suitable sealing coats, include, but are not limited to, HPMC (hydroxypropylmethylcellulose) such as Seppifilm™, Opadry® AMB (polyvinyl alcohol and lecithin), and Kollicoat® Protect (polyvinyl alcohol-polyethylene glycol copolymer and polyvinyl alcohol). Any other suitable sealing coat known to those skilled in the art may be used.

In some embodiments, formulations of the invention may comprise a top coat around the outside of the bead. These formulations may also comprise a sealing coat. For example, an embodiment of this type might comprise a core particle, a drug layer, a sealing coat, a polymer coat and a top coat.

In some embodiments of the invention, the drug layer may comprise a non-reducing sugar (e.g., trehalose) as a binder. A formulation of this type might comprise a core particle, a tight-junction-effector-containing layer that also comprises trehalose, and a delayed-release polymer layer. Such a formulation might further comprise a sealing layer over the tight-junction-effector-containing layer and/or a top coat layer over the delayed-release layer as described above.

The delayed-release coat (e.g., a coat comprising Eudragit L30D55) may be formulated using any techniques known in the art. In some embodiments, the delayed-release coating may comprise talc. Talc may be present as from about 0.5% to about 15%, from about 1% to about 15%, from about 2% to about 15%, from about 3% to about 15%, from about 4% to about 15%, from about 5% to about 15%, from about 6% to about 15%, from about 7% to about 15%, from about 8% to about 15%, from about 9% to about 15%, from about 10% to about 15%, from about 11% to about 15%, from about 12% to about 15%, from about 13% to about 15%, from about 14% to about 15% by weight of the solution used to apply the coat. Thus, the solution used to apply the delayed-release coat may comprise about 0.5%, about 1%, about 2%, about 3%, about 4%, about 5%, about 6%, about 7%, about 8%, about 9%, about 10%, about 11%, about 12%, about 13%, about 14% or about 15% talc by weight.

Formulations of the invention may further comprise one or more additives that may be applied to the beads after the application of a delayed-release coat, after the application of any top coat, after the drug layer, or in lieu of the enteric coat, all as non-limiting examples. Such additives may comprise one or more agents to impart desired dissolution or other characteristics, non-limiting examples of which as disclosed in Asghar et al, J Pharm Pharm Sci (2006) 9(3) pages 327-338. Such examples include means of obtaining different pH-dependent release (such as Eudragit L-100, Eudragit S-100, cellulose acetate phthalate (CAP), shellac, ethyl cellulose), time-dependent release (e.g. hydroxy propyl methyl cellulose, hydroxyethyl cellulose, microcrystalline cellulose, lactose/behinic acid, hydroxy propyl methyl cellulose, hydroxy propyl methyl cellulose acetate succinate) or release dependent on bacteria (e.g. chitosan, pectin, guar gum, chondroitin sulphate, amylose, alginates). Other additives may include agents to make the mixture more uniform, for example, silicon dioxide or syloid. All of the above are non-limiting examples of agents known in the art All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An oral dosage composition comprising an effective amount of Larazotide acetate (AT1001), and comprising first delayed-release particles capable of releasing Larazotide acetate in the duodenum of a patient, and second delayed-release particles capable of releasing Larazotide acetate in the jejunum of a patient,
wherein:
the first delayed-release particles comprise:
a first core particle;
a coat comprising Larazotide acetate over the first core particle; and
a delayed-release coating outside the coat comprising Larazotide acetate, the delayed-release coating comprising a co-polymer of acrylate or methacrylate, and being stable in simulated gastric fluid and releasing at least 70% of the Larazotide acetate in the first delayed-release particles by about 60 minutes of exposure to simulated intestinal fluid having a pH of greater than 5; and
the second delayed-release particles comprise:
a second core particle;
a coat comprising Larazotide acetate over the second core particles; and
a delayed-release coating outside the coat comprising Larazotide acetate, the delayed-release coating comprising a co-polymer of acrylate or methacrylate, and being stable in simulated gastric fluid and releasing at least 70% of the Larazotide acetate in the second delayed-release particles by about 30 and about 90 minutes of exposure to simulated intestinal fluid having a pH of greater than 5.

2. The composition of claim 1, wherein the first and second core particles have an average size of from 15 to 40 mesh.

3. The composition of claim 1, wherein the core particle material comprises an oxide, cellulose, a polymer, an inorganic salt, or a sugar.

4. The composition of claim 1, wherein the core particle material is a sugar.

5. The composition of claim 1, wherein the delayed-release coatings comprise polymethacrylate.

6. The composition of claim 5, wherein the polymethacrylate is a 1:1 copolymer of polymethacrylic acid and ethyl acrylate.

7. The composition of claim 1, further comprising a sealing coat disposed over the coats comprising Larazotide acetate.

8. The composition of claim 7, wherein the sealing coat comprises sugar, polyethylene glycol, polyvinylpyrrolidone, polyvinyl alcohol, polyvinyl acetate, hydroxypropyl cellulose, methylcellulose, ethylcellulose, and/or hydroxypropylmethylcellulose (HPMC).

9. The composition of claim 7, wherein the sealing coat comprises HPMC.

10. The composition of claim 1, further comprising a top coat around the outside of the first delayed-release particles and the second delayed-release particles.

11. The composition of claim 10, wherein the top coat comprises sugar, polyethylene glycol, polyvinylpyrrolidone, polyvinyl alcohol, polyvinyl acetate, hydroxypropyl cellulose, methylcellulose, ethylcellulose, and/or hydroxypropylmethylcellulose (HPMC).

12. The composition of claim 10, wherein the sealing coat comprises HPMC.

13. The composition of claim 1, wherein the coats comprising Larazotide acetate further comprise a pharmaceutically-acceptable binder.

14. The composition of claim 13, wherein the binder comprises a natural sugar, starch, gelatin, corn sweetener, gum, carboxymethylcellulose, polyvinyl pyrrolidone, hydroxypropyl cellulose, hydroxyethyl cellulose, ethylcellulose, polymethacrylate, polyethylene glycol, or wax.

15. The composition of claim 13, wherein the binder comprises sugar.

16. The composition of claim 1, wherein the delayed-release coatings further comprise talc.

17. The composition of claim 1, further comprising an inert processing aid and/or plasticizer.

18. The composition of claim 17, wherein the inert processing aid comprises silicon dioxide, talc, and/or magnesium stearate.

19. The composition of claim 17, wherein the plasticizer comprises citric acid ester, triacetin, phthalic acid ester, dibutyl sebacate, cetyl alcohol, polyethylene glycol, and/or polysorbate.

20. The composition of claim 1, wherein the composition is a capsule.

21. The composition of claim 9, wherein:
the delayed-release coating of the first delayed-release particle comprises a 1:1 methacrylic acid-ethyl acrylate copolymer, and is about 20% of the weight of the first particle having the coat comprising Larazotide acetate over the first particle; and
the delayed-release coating of the second delayed-release particle comprises a 1:1 methacrylic acid-ethyl acrylate copolymer, and is about 70% of the weight of the second particle having the coat comprising Larazotide acetate over the second particle.

22. The composition of claim 1, wherein the simulated gastric fluid and simulated intestinal fluid do not contain enzymes.

23. The composition of claim 21, wherein the composition comprises the Larazotide acetate at from 0.1% to about 6% based on the total weight of the composition.

24. The composition of claim 1, wherein the simulated gastric fluid has a pH of about 1.2.

25. The composition of claim 24, wherein less than 10% of the Larazotide acetate is released in the presence of simulated gastric fluid in approximately 60 minutes.

26. An oral dosage composition comprising a population of delayed-release particles containing Larazotide acetate (AT1001), the population of delayed release particles consisting of first delayed-release particles capable of releasing Larazotide acetate in the duodenum of a patient, and second delayed-release particles capable of releasing Larazotide acetate in the jejunum of a patient,
wherein:
the first delayed-release particles comprise:
a first core particle;
a coat comprising Larazotide acetate over the first core particle; and
a delayed-release coating outside the coat comprising Larazotide acetate, the delayed-release coating comprising a co-polymer of acrylate or methacrylate, and being stable in simulated gastric fluid and releasing at least 70% of the Larazotide acetate in the first delayed-release particles by about 60 minutes of exposure to simulated intestinal fluid having a pH of greater than 5; and
the second delayed-release particles comprise:
a second core particle;
a coat comprising Larazotide acetate over the second core particles; and
a delayed-release coating outside the coat comprising Larazotide acetate, the delayed-release coating comprising a co-polymer of acrylate or methacrylate, and being stable in simulated gastric fluid and releasing at least 70% of the Larazotide acetate in the second delayed-release particles by about 30 and about 90 minutes of exposure to simulated intestinal fluid having a pH of greater than 5.

27. The oral dosage composition of claim 1, wherein the simulated intestinal fluid has a pH of 6.8.

28. The oral dosage composition of claim 26, wherein the simulated intestinal fluid has a pH of 6.8.

* * * * *